United States Patent [19]

Ichimura

[11] 4,287,335
[45] Sep. 1, 1981

[54] NITROGEN-CONTAINING HETEROCYCLIC COMPOUND HAVING ACETAL GROUP AND METHOD FOR MANUFACTURE THEREOF

[75] Inventor: Kunihiro Ichimura, Yokohama, Japan

[73] Assignees: Agency of Industrial Science & Technology; Ministry of International Trade & Industry, both of Tokyo, Japan

[21] Appl. No.: 162,834

[22] Filed: Jun. 25, 1980

[30] Foreign Application Priority Data

Jul. 4, 1979 [JP] Japan .................................. 54-84817

[51] Int. Cl.$^3$ ................. C07D 213/30; C07D 215/10; C07D 405/10
[52] U.S. Cl. ...................................... 542/455; 525/61
[58] Field of Search ........................................ 542/455

[56] References Cited

U.S. PATENT DOCUMENTS

| | | | |
|---|---|---|---|
| 2,255,077 | 9/1941 | Middleton | 542/455 |
| 3,152,042 | 10/1964 | Wood et al. | 542/455 |
| 3,382,076 | 5/1968 | Kalenda | 542/455 |
| 3,382,240 | 5/1968 | Iwai et al. | 542/455 |
| 3,705,895 | 12/1972 | Levy et al. | 542/455 |

OTHER PUBLICATIONS

Ichimura et al., Chem. Lett., 1978, pp. 1289–1292.

*Primary Examiner*—Arthur P. Demers
*Attorney, Agent, or Firm*—Oblon, Fisher, Spivak, McClelland & Maier

[57] ABSTRACT

A novel compound represented by the general formula:

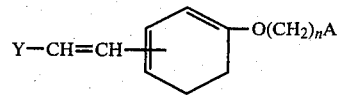

[wherein, A is one member selected from the group consisting of

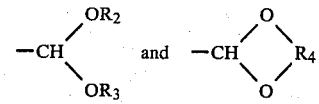

(where $R_2$ and $R_3$ are each an alkyl group and $R_4$ is an alkylene group), Y is one member selected from the group consisting of

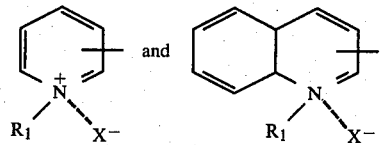

(where $R_1$ is one member selected from the class consisting of alkyl group, aryl group and aralkyl group)] is obtained by causing a compound of the general formula:

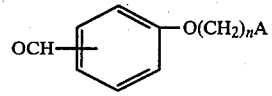

(wherein, A and n have the same meaning as described above) to react with a compound of the general formula:

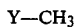

(wherein, Y has the same meaning as described above).

5 Claims, No Drawings

NITROGEN-CONTAINING HETEROCYCLIC COMPOUND HAVING ACETAL GROUP AND METHOD FOR MANUFACTURE THEREOF

BACKGROUND OF THE INVENTION

This invention relates to a novel styrylpyridinium salt or a novel styrylquinolinium salt containing an acetal group useful for the preparation of a water-soluble highly photosensitive resin and to a method for the manufacture of the salt.

Water-soluble photosensitive resins are used in low-pollution type photoresists and photomilling materials. Recently, these photosensitive resins have come to receive attention for their usefulness as immobilizing carriers for enzymes and other bioactive substances.

As a photosensitive high-molecular compound suitable for such new uses, the inventors earlier developed a polymer possessing a stilbazolium residue [Refer to Ichimura & Watanabe: Chem., Lett., 1289 (1978)]. They continued a study with a view to imparting enhanced water solubility and improved photosensitivity to the polymer possessing the stilbazolium residue. They have, consequently, discovered that a water-soluble highly photosensitive resin can be obtained by using a method for incorporating a stilbazolium group into poly(vinyl alcohol) through the reaction of acetalization (U.S. Application Ser. No. 62,490, dated July 31, 1979).

SUMMARY OF THE INVENTION

The inventors have devoted a diligent study to the development of a compound possessing a styrylpyridinium group or a styrylquinolinium group suitable for the reaction of acetalization and, consequently, have succeeded in developing a novel nitrogen-containing heterocyclic compound possessing a styryl group and a method for the manufacture of the compound.

Specifically, the novel compound of the present invention is a nitrogen-containing heterocyclic compound represented by the general formula:

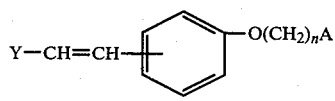
(I)

wherein, Y is one member selected from the group consisting of

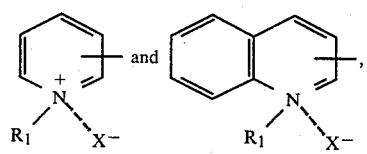

A is one member selected from the group consisting of

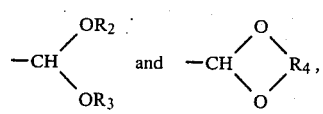

n is an integer having the value of 1 to 6, X is a strongly acidic anionic residue and, in the substituents Y and A, $R_1$ is one member selected from the group consisting of an alkyl group, aryl group and aralkyl group, $R_2$ and $R_3$ are each an alkyl group, and $R_4$ is an alkylene group.

The nitrogen-containing heterocyclic compound represented by the formula (I) is prepared by the reaction of a benzaldehyde derivative represented by the general formula:

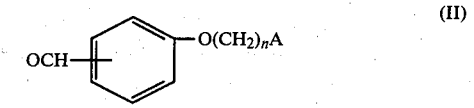
(II)

and a compound represented by the general formula:

$Y-CH_3$ (III).

In the formulas (II) and (III), A and Y have the same meanings as used in the formula (I) above.

An object of the present invention is to provide a novel nitrogen-containing heterocyclic compound possessing a styryl group highly suitable for the incorporation of a styrylpyridinium group or a styrylquinolinium group directed to imparting photosensitivity to polymers.

Another object of this invention is to provide a method for the manufacture of the nitrogen-containing heterocyclic compound described above.

DESCRIPTION OF THE PREFERRED EMBODIMENTS

The aldehyde possessing an acetal group, represented by the general formula,

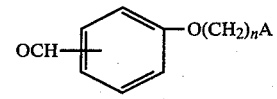

(II), and used as the raw material in the method of the present invention is obtained by causing an acetal of the general formula:

$X'(CH_2)_nA$ (IV)

(wherein, X' denotes a halogen atom, alkanesulfonyloxy group or arenesulfonyloxy group, and A and n have the same meanings as described above) to react thermally with hydroxybenzaldehyde under an alkaline condition.

The conditions under which the thermal reaction is effectively carried out are as follows.

The molar ratio of acetal to hydroxybenzaldehyde is within the range of 1:0.5~2. The thermal reaction is carried out at temperatures within the range of from 50° to 200° C. for a period of from one to 24 hours. The molar ratio of hydroxybenzaldehyde to alkali in the reaction solution is about 1:1~1.5.

The reaction between the benzaldehyde possessing an acetal group and represented by the general formula (II) which is obtained as described above and the compound represented by the general formula (III) can be advantageously carried out in a polar solvent such as, for example, methanol, ethoxyethyl alcohol or ethanol. Normally this reaction is performed at temperatures within the range of from room temperature to 100° C. for a period of from 30 minutes to 20 hours. In this case, it is advantageous to avoid performing this reaction at excessively high temperatures or for a prolonged period of time.

When the reaction temperature is lower or the reaction time shorter than the respective ranges mentioned above, the reaction proceeds very slowly. When the reaction temperature is higher or the reaction time longer than the respective ranges, however, the reaction produces a heavily colored resinous product, with the result that the product is difficult of isolation and purification and the yield of the reaction itself is lowered. In the reaction, it is important that the molar ratio of the compound (II) to the compound (III) should fall within the range of 1:0.5~1. When the amount of the compound (III) fails to reach the lower limit of the aforementioned range, the amount of the compound (II) which remains unaltered after the reaction is so large as to jeopardize the economy of the reaction. When it exceeds the upper limit of the range, the unaltered portion of the compound (III) mingles into the reaction product at the time that the product is isolated from the reaction mixture, making the purification of the product highly complicated.

To accelerate the reaction, there is used a basic catalyst. Aliphatic amines and the acetates thereof are preferably used as the catalyst.

Concrete examples of catalysts which are advantageously used for this reaction include pyrrolidine, piperidine, diethylamine and triethylamine. The amount in which the catalyst is added to the reaction system is within the range of from 0.1 to 5 mol% based on the combined amount of the reactants (II) and (III).

Practical examples of the residues $R_1$, $R_2$, $R_3$ and $R_4$ involved in the general formulas of the reactants are as follows:

$R_1$-Methyl, ethyl, propyl, butyl and benzyl
$R_2$, $R_3$-Methyl, ethyl and propyl
$R_4$-Ethylene, 1,3-propylene and 1,2-propylene Examples of benzaldehyde derivatives possessing an acetal group and represented by the general formula (II) are o-(2,2-dimethoxyethoxy)benzaldehyde, m-(2,2-dimethoxyethoxy)benzaldehyde, p-(2,2-dimethoxyethoxy)benzaldehyde, p-(2,2-diethoxyethoxy)benzaldehyde, p-(3,3-dimethoxypropoxy)benzaldehyde, p-(4,4-diethoxybutoxy)benzaldehyde, p-(5,5-dimethoxypentoxy)benzaldehyde, p-(6,6-dimethoxyhexyloxy)benzaldehyde, m-(2,2-ethylenedioxyethoxy)benzaldehyde, p-(3,3-propylenedioxypropoxy)benzaldehyde and p-(5,5-ethylenedioxypentoxy)benzaldehyde.

Concrete examples of the substituent $X^-$ in the compound of the aforementioned general formula (III) are halogen ions, sulfuric acid ion, methyl sulfate ion, phosphoric acid ion, methanesulfonate ion, and p-toluenesulfonate ion. Specific examples of the compounds containing such substituents are chlorides, bromides, iodides, methyl sulfates, methanesulfonates and p-toluenesulfonates of pyridinium and quinolium such as 1,2-dimethylpyridinium, 1,4-dimethylpyridinium, 1-ethyl-4-methylpyridinium, 1-butyl-4-methylpyridinium, 1-benzyl-4-methylpyridinium, 1-(2-hydroxyethyl)-2-methylpyridinium, 1-(2-hydroxyethyl)-4-methylpyridinium, 1,2-dimethylquinolinium, 1,4-dimethylquinolinium and 1-ethyl-4-methylquinolinium. The above mentioned quaternary salts may be those incorporating lower alkyl and hydroxy groups having up to about six carbon atoms on condition that the presence thereof does not interfere with the condensation reaction.

The nitrogen-containing heterocyclic compound possessing an acetal group and represented by the aforementioned general formula,

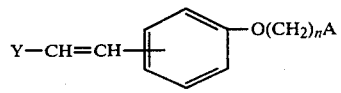

(I), which is obtained by the method described above is a crystalline substance. This compound, when exposed by itself to light for a long time, undergoes a change presumably originating in photodimerization reaction. It is, therefore, desired to be stored in a place shielded from light of short wavelength.

The chemical structure of the novel nitrogen-containing heterocyclic compound represented by the aforementioned general formula (I) has been determined on the basis of the results of elementary analysis, infrared absorption spectrum and ultraviolet absorption spectrum.

The nitrogen-containing heterocyclic compound of the present invention which is represented by the aforementioned general formula (I), when allowed to react with poly(vinyl alcohol) or a partially saponified poly(vinyl acetate), efficiently produces a photosensitive resin of a poly(vinyl alcohol) derivative possessing a structural unit of the general formula:

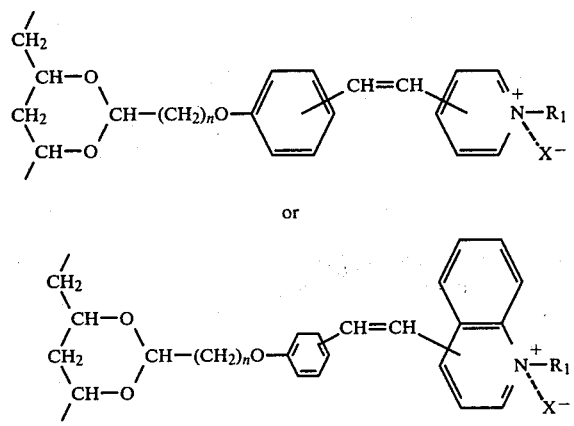

(wherein, $R_1$, $X^-$ and n have the same meanings as described above). Specifically, use of the nitrogen-containing heterocyclic compound possessing an acetal group obtained by the present invention permits a wide choice of the N-substituent and promises easy adaptation of the physical and chemical properties of the photosensitive resin, as the final product, to suit the particular application for which the resin is intended. The production of the aforementioned photosensitive resin can be carried out in water in the presence of an acidic catalyst. The reaction brings about a water-soluble, highly photosensitive resin.

Typical photosensitive resins containing the nitrogen-containing heterocyclic compound of the present invention are cited below, with the properties of the resins indicated correspondingly.

| Kind of resin matrix Poly(vinyl alcohol) (PVA) | | | Properties of photosensitive resin | |
| --- | --- | --- | --- | --- |
| Polymerization degree | Saponification degree | Nitrogen-containing heterocyclic compound Structure | Amount added based on vinyl unit of PVA | Relative sensitivity* |
| 1700 | about 87% | 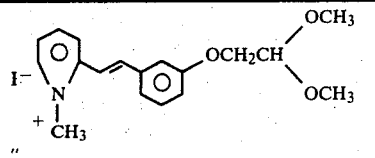 | 0.8 mol % | 2.2 |
| " | " | " | 1.4 mol % | 6.5 |
| " | " | " | 0.75 mol % | 3.7 |
| " | " | 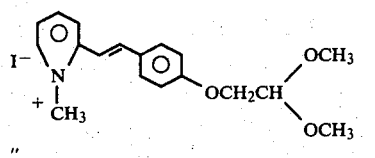 | | |
| " | " | " | 1.3 mol % | 8.5 |
| " | " | " | 1.1 mol % | 10.2 |
| " | " | 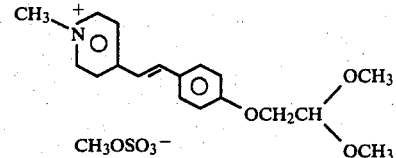 | | |
| " | " | " | 2.1 mol % | 30 |
| " | " | " | 0.53 mol % | 7 |
| " | " | 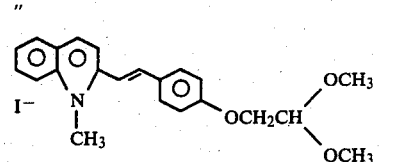 | | |

*Based on the sensitivity (as unity) which is exhibited by a poly(vinyl alcohol) (polymerization degree 1700 and saponification degree about 87%) containing 6 w/w % of ammonium dichromate. The development was invariably made in water.

Now, the present invention will be described below specifically with reference to working examples.

The first two examples concern the preparation of benzaldehyde derivatives.

EXAMPLE 1

In 50 ml of methanol, 50 g of p-hydroxybenzaldehyde and 23 g of potassium hydroxide were dissolved. The resultant solution was distilled under a vacuum to expel the solvent. The residue of the distillation was dried under a vacuum. This dry residue was dissolved by heating in 60 ml of N-methyl pyrrolidone. In the resultant solution, 76.5 g of chloroacetaldehyde dimethyl acetal was heated at 150° C. for 15 hours. The reaction solution was combined with 200 ml of dichloromethane and washed three times with water and was further washed with 100 ml of an aqueous 10% sodium hydroxide solution to recover the unaltered portion of hydroxybenzaldehyde. Next the so-obtained organic phase was washed with water, dried with anhydrous potassium carbonate and distilled to extract N-methyl pyrrolidone, whereafter p-(2,2-dimethoxyethoxy)benzaldehyde was extracted at 135° C./3 mmHg. When the extracts thus obtained were distilled again, there was obtained 34.2 g of a colorless liquid of p-(2,2-dimethoxyethoxy)benzaldehyde at 145° C./3 mmHg.

EXAMPLE 2

In 20 ml of 2-ethoxyethyl alcohol, 1.65 g of sodium hydroxide and 4.88 g of m-hydroxybenzaldehyde were dissolved by heating. The resultant solution and 7.4 g of bromoacetaldehyde dimethyl acetal were refluxed for 22 hours. Then, the reaction solution was combined with 50 ml of benzene, washed with water, and further washed with an aqueous sodium hydroxide solution until total disappearance of the unaltered portion of hydroxybenzaldehyde and thereafter dried with anhydrous potassium carbonate. By distilling the resultant aqueous solution, there was obtained 3.6 g of m-(2,2-dimethoxyethoxy)benzaldehyde with a boiling point of 138° C./3 mmHg.

When the procedure described above was repeated, except that the m-hydroxybenzaldehyde was replaced with the same amount of o-hydroxybenzaldehyde, there was obtained 3.4 g of o-(2,2-dimethoxyethoxy)benzaldehyde with a boiling point of 147° C./5 mmHg.

The following five examples concern the method of this invention for the preparation of the novel nitrogen-containing heterocyclic compound.

EXAMPLE 3

In 10 ml of ethanol, 5.4 g of 1,4-dimethyl pyridinium.p-toluene sulfonate and 3.7 g of p-(2,2-dimethoxyethoxy)benzaldehyde were dissolved. The resultant solution, with five drops of piperidine added thereto, was refluxed for 30 minutes. The resultant dark green reaction solution, with acetone added thereto and then ethyl acetate further added thereto, was left to stand. The crystals which deposited during this standing were collected and washed with acetone. Consequently, there was obtained 1.75 g of 1-methyl-4-[p-(2,2-dimethoxyethoxy)-styryl]pyridinium.p-toluene sulfonate with a boiling point of 219°∼226° C. The ultraviolet absorption spectrum of this product in water was 370 nm ($\epsilon=3.26\times10^4$). The infrared absorption spectrum (KBr) showed peaks at 1620, 1600, 1512, 1470, 1260, 1220, 1180, 1140, 1120, 1075, 1030, 1008, 975, 832, 815 and 675 cm$^{-1}$. The yield was 32%.

EXAMPLE 4

In 6 ml of methanol, 1.50 g of 1,2-dimethylpyridinium iodide and 1.50 g of o-(2,2-dimethoxyethoxy)benzaldehyde. The resultant solution, with two drops of piperidine added thereto, was refluxed for five hours and then left to stand and cool off. The crystals which deposited consequently were collected and thoroughly washed with acetone. Consequently, there was obtained 2.36 g of 1-methyl-2-[o-(2,2-dimethoxyethoxy)-styryl]-pyridinium iodide which melted at 169°~173° C. This product showed the highest absorption at 353 nm ($\epsilon=1.78\times10^4$). The infrared absorption spectrum (KBr) showed peaks at 1630, 1610, 1595, 1567, 1515, 1500, 1450, 1280, 1248, 1130, 1065, 971, 780, 760 and 750 cm$^{-1}$. The yield was 87%.

EXAMPLE 5

In 6 ml of methanol, 1.50 g of 1,2-dimethyl pyridinium iodide and 1.50 g of m-(2,2-dimethoxyethoxy)-benzaldehyde were dissolved. The resultant solution, with two drops of piperidine added thereto, was refluxed for five hours and thereafter cooled off. Consequently, crystals were deposited. When the crystals were collected and washed thoroughly with acetone, there was obtained 2.34 g of 1-methyl-2-[m-(2,2-dimethoxyethoxy)-styryl]pyridinium iodide. In water, this product showed the highest absorption at 336 nm ($\epsilon=2.13\times10^4$). The infrared absorption spectrum (KBr) showed peaks at 1620, 1600, 1580, 1268, 1137, 1068, 965, 840, 772 and 680 cm$^{-1}$. The yield was 86%.

EXAMPLE 6

In 50 ml of methanol, 12.7 g of 1,2-dimethylpyridinium iodide and 11.96 g of p-(2,2-dimethoxyethoxy)benzaldehyde were dissolved. The resultant solution, with 1 ml of piperidine added thereto, was refluxed for five hours. The solution was left to cool and the crystals which consequently deposited in the solution were collected through filtration and thoroughly washed with acetone. Consequently, there was obtained 16.30 g of 1-methyl-2[p-(2,2-dimethoxyethoxy)-styryl]-pyridinium iodide. In water, this product showed the highest absorption at 360 nm ($\epsilon=2.67\times10^4$). The infrared absorption spectrum (KBr) of the product showed peaks at 1630, 1615, 1595, 1568, 1512, 1450, 1298, 1260, 1180, 1140, 1073, 965, 862, 821 and 776 cm$^{-1}$. The yield was 67%.

EXAMPLE 7

In 20 ml of methanol, 4.28 g of 1,2-dimethylquinolinium iodide and 3.47 g of p-(2,2-dimethoxyethoxy)benzaldehyde were dissolved. The resultant solution, with 0.3 ml of piperidine added thereto, was refluxed for seven hours. The solution was left to cool. The crystals which consequently deposited were collected through filtration and then washed thoroughly with acetone. Consequently, there was obtained 5.03 g of 1-methyl-2-[p-(2,2-dimethoxyethoxy)-styryl]-quinolinium iodide which boiled at 209°~212° C. This product in water showed absorption bands ($\lambda_{max}$) at 224, 255, 307 and 399 nm. The infrared absorption spectrum (KBr) showed peaks at 1610, 1590, 1572, 1516, 1240, 1180, 1130, 1068, 985, 830, 780 and 760 cm$^{-1}$.

What is claimed is:

1. A nitrogen-containing heterocyclic compound represented by the formula:

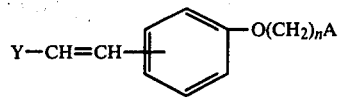

wherein, Y is one member selected from the group consisting of

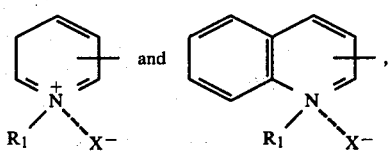

A is one member selected from the group consisting of

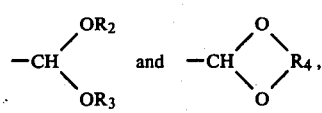

and n is an integer of 1 to 6, providing that in the formulas of Y and A, $R_1$ is one member selected from the group consisting of alkyl, aryl and aralkyl, $R_2$ and $R_3$ are each an alkyl group, $R_4$ is an alkylene group and $X^-$ is a strongly acidic anionic residue.

2. The compound according to claim 1, wherein the substituent $X^-$ in the general formula of Y is one member selected from the group consisting of halogen ions, sulfuric acid ion, methyl sulfate ion, phosphoric acid ion, methane sulfonate ion and p-toluenesulfonate ion.

3. The compound according to claim 1, wherein said Y substituent is 1,2-dimethylpyridinium, 1,4-dimethylpyridinium, 1-ethyl-4-methylpyridinium, 1-butyl-4-methylpyridinium, 1-benzyl-4-methylpyridinium, 1-(2-hydroxyethyl)-2-methylpyridinium, 1-(2-hydroxyethyl)-4-methylpyridinium, 1,2-dimethylquinolinium, 1,4-dimethylquinolinium or 1-ethyl-4-methylquinolinium.

4. The compound according to claim 1, wherein said substituent A is —CH(OCH$_3$)$_2$, —CH(OCH$_2$CH$_3$)$_2$,

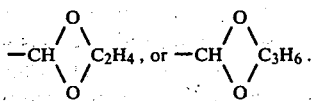

5. The compound according to claim 1, wherein said $R_1$ substituent is methyl, ethyl, propyl, butyl or benzyl, said $R_2$ and $R_3$ substituents are methyl, ethyl and propyl and said $R_4$ is ethylene, 1,3-propylene or 1,2-propylene.

* * * * *